United States Patent [19]
Yokoshima et al.

[11] 4,452,996
[45] Jun. 5, 1984

[54] DI(METH)ACRYLATE ESTERS OF HYDROXYPIVALYL HYDROXYPIVALATE ε-CAPROLACTONE CONDENSATES

[75] Inventors: Minoru Yokoshima, Yamaguchi; Kazuyoshi Nawata, Onoda; Tetsuo Hironaka, Ube; Hideaki Takahashi, Yamaguchi, all of Japan

[73] Assignee: Nippon Kayaku Kabushiki Kaisha, Japan

[21] Appl. No.: 461,640

[22] Filed: Jan. 27, 1983

[30] Foreign Application Priority Data

Feb. 13, 1982 [JP]  Japan ................................. 57-20687

[51] Int. Cl.$^3$ ..................... C07C 69/675; C07C 69/73
[52] U.S. Cl. ............................... 560/185; 204/159.16; 526/323.1; 526/323.2; 260/DIG. 38
[58] Field of Search ................. 560/185, 183; 106/20; 204/159.16

[56] References Cited

U.S. PATENT DOCUMENTS

3,759,862  9/1973  Fukui et al. .......................... 560/185
3,914,177  10/1975  Nahta et al. ......................... 560/185

Primary Examiner—Glennon H. Hollrah
Assistant Examiner—L. Hendriksen
Attorney, Agent, or Firm—Henry C. Nields

[57] ABSTRACT

Di(meth)acrylate esters of the formula:

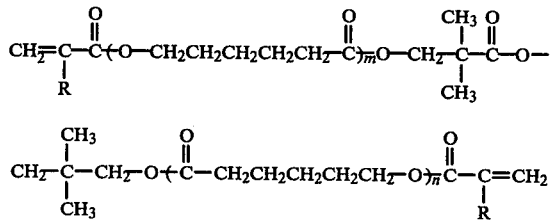

wherein m and n each represents O or an integer of 1 to 3, the average sum of m+n being 1 to 6 and R represents hydrogen or a methyl group, and process for producing the same.

The esters are copolymerizable with other unsaturated compounds to form radiation hardenable films with a reduced irritating effect.

5 Claims, No Drawings

DI(METH)ACRYLATE ESTERS OF HYDROXYPIVALYL HYDROXYPIVALATE ε-CAPROLACTONE CONDENSATES

DETAILED DESCRIPTION OF THE INVENTION

The present invention relates to new di(meth)acrylate esters easily copolymerizable with unsaturated group-containing resins in the presence of heat, UV rays, ionizing radiation or radical initiator.

Radiation-curing compositions, particularly paint and printing ink compositions are well known. Efforts have been made in the art for the purpose of obtaining a completely polymerizable composition free of volatile matter and comprising components which per se constitute the whole or part of cured film, since allowable solvent content of the atmosphere is limited, energy cost required for the evaporation of solvent has been increased and cost of the solvent per se has been increased. As is well known, acrylate esters are used as reactive diluents in place of solvents. The selection of acrylate esters to be used as the diluent and amount (ratio) thereof are important. For example, neopentyl glycol diacrylate and 1,6-hexanediol diacrylate are not preferred, since they exhibit a strong irritation effect in handling, although they can reduce the viscosity of the resin effectively. Pentaerythritol triacrylate having a high viscosity has a defect that it should be used in a large amount relative to the resin when it is used as the diluent and, therefore, properties of the resin are deteriorated.

After intensive investigations, the inventors have succeeded in obtaining new di(meth)acrylate esters having a remarkably reduced irritating effect and a relatively low viscosity. The present invention relates to new di(meth)acrylate esters of the general formula [I]:

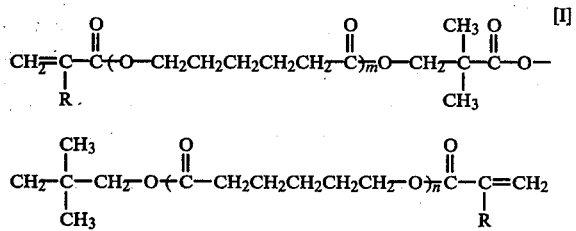

wherein m and n each represents 0 or an integer of 1 to 3, the average sum of m+n being 1 to 6, preferably 2 to 4 and R represents hydrgen or a methyl group.

These new di(meth)acrylate esters [I] are prepared preferably by reacting a condensate [II] of hydroxypivalyl hydroxypivalate and ε-caprolactone of the general formula [II]:

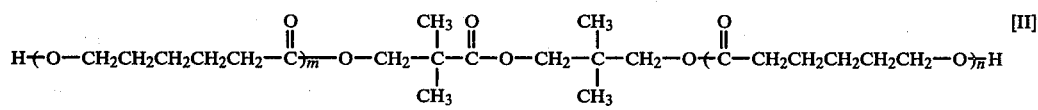

wherein the symbols have the same meaning as in formula [I], with acrylic acid or methacrylic acid under heating. This reaction will be described below in detail. The condensate of hydroxypivalyl hydroxypivalate and ε-caprolactone of the general formula [II] is prepared by reacting hydroxypivalyl hydroxypivalate with ε-caprolactone.

PREPARATION OF CONDENSATE OF HYDROXYPIVALYL HYDROXYPIVALATE AND ε-CAPROLACTONE (GENERAL FORMULA [II])

It is preferred to use a catalyst in a catalytically effective amount in the reaction of hydroxypivalyl hydroxypivalate with ε-caprolactone. The amount of the catalyst is 0.001 to 1.0 wt%, preferably 0.01 to 0.2 wt%, based on caprolactone. Useful catalysts are those known by those skilled in the field of lactone adducts chemistry. As examples of the useful catalysts, there may be mentioned organotitanium compounds such as tetraisopropyl titanate and tetrabutyl titanate and tin compounds such as tetraphenyltin, tetraoctyltin, diphenyltin dilaurate, dilauryltin oxide and di-n-butyltin dichloride. The reaction of hydroxypivalyl hydroxypivalate with ε-caprolactone is carried out at 50° to 300° C., preferably 130° to 200° C., for a time sufficient for completing the reaction of the reactants. The amount of ε-caprolactone charged in the reaction system is 1 to 6 mol, preferably 2 to 4 mol, per mol of hydroxypivalyl hydroxypivalate. For minimizing side oxidation reaction, it is preferred that the reaction is carried out in an inert gas atmosphere such as nitrogen. After completion of the reaction, the resulting mixture comprising the condensate of hydroxypivalyl hydroxypivalate and ε-caprolactone may be used as it is.

PREPARATION OF DI(METH)ACRYLATE ESTER (GENERAL FORMULA [I]

A di(meth)acrylate ester (general formula [I]) is prepared by reacting the condensate of hydroxypivalyl hydroxypivalate and ε-caprolactone (general formula [II]) with acrylic acid, methacrylic acid or a mixture of them. The amount of acrylic acid or methacrylic acid is about 2 to 4 mol per mol of the condensate of hydroxypivalyl hydroxypivalate and ε-caprolactone (general formula [II]) charged. It is desirable that 2 mol (stoichiometrical amount) of acrylic or methacrylic acid or a mixture of them is reacted with reactive hydrogen atoms of hydroxyl groups of the condensate of hydroxypivalyl hydroxypivalate and ε-caprolactone (general formula [II]). However, in practice, it is preferred to charge a slightly excess amount of them to carry out the reaction completely. The reaction is carried out preferably in the presence of a polymerization inhibitor to minimize or retard the polymerization of the acrylic double bonds. The polymerization inhibitors are those known in the art and they are used in a concentration of 0.01 to 5 wt% based on the mixture. As examples of the polymerization inhibitors, there may be mentioned hydroquinone, p-methoxyphenol, 2,4-dimethyl-6-t-butylphenol, 3-hydroxythiol, α-nitroso-β-naphthol, p-benzoquinone, phenothiazine, N-nitrosodiphenylamine and copper salts. The reaction is carried out generally at about 50° to 130° C., preferably 65° to 90° C., for a time sufficient to ensure the completion of the esterification of the condensate of hydroxypivalyl hydroxypivalate and ε-caprolactone (general formula [II]) with acrylic acid or methacrylic acid to form the di(meth)acrylate ester (general formula [I]). The time varies depending on the batch scale, respective reactants, catalyst and reaction conditions employed. An esterification catalyst is also used in a concentration of 0.1 to 15 molar %, preferably 1 to 6 molar %, based on acrylic acid or methacrylic acid used. Any of known esterification catalysts may be used. As examples of the catalysts, there may be mentioned p-toluenesulfonic acid, methanesulfonic acid, phosphoric acid and sulfuric acid. It is desirable to use an inert solvent such as hexane, cryclohexane, benzene or toluene to promote the removal of water formed in the course of the esterification reaction. The radiation-curable composition containing the di(meth)acrylate ester (general formula [I]) and the unsaturated group-containing resin can be cured by means of heat, U.V. rays, ionizing radiation, or radical initiator (preferably by means of U.V. rays). In case the curing is effected by U.V. rays, 0.1 to 10 wt% of a photopolymerization initiator or sensitizer is incorporated in the composition. They are well-known compounds and include, for example, benzyl ketal, benzoin isopropyl ether, benzoin isobutyl ether, benzophenone, acetophenone, di-sec-butoxyacetophenone, xanthone, thioxanthone, benzaldehyde and anthraquinone. As examples of the unsaturated group-containing resins usable in combination with the di(meth)acrylate esters (general formula [I]), there may be mentioned epoxy acrylates such as epoxidized bisphenol A acrylate, epoxydized linseed oil acrylate and epoxidized soybean oil acrylate; unsaturated polyesters containing saturated and unsaturated carboxylic acids such as maleic acid, fumaric acid and adipic acid; diisocyanates and polyisocyanates; and urethane acrylates obtained by the reaction of hydroxyalkyl acrylates. The di(meth)acrylate ester (general formula [I])-containing composition of the present invention may be applied to any of suitable substrates such as wood, metal, glass, fabric, paper, fiber and plastic having any shape such as sheet, coil, molded article, film, panel or pipe.

In a typical embodiment of the invention, acrylic acid, hydroxypivalyl hydroxypivalate/ε-caprolactone condensate (general formula [II]), catalyst, solvent and polymerization inhibitor are charged in a reactor and heated until the esterification reaction has substantially been completed and the formed di(meth)acrylate ester [I] is recovered by a conventional method.

Now the present invention will be illustrated by means of synthesis examples of hydroxypivalyl hydroxypivalate/ε-caprolactone condensate and further by means of examples. Parts are given by weight, unless otherwise stated.

SYNTHESIS OF HYDROXYPIVALYL HYDROXYPIVALATE/ε-CAPROLACTONE CONDENSATE

SYNTHESIS EXAMPLE 1

408.4 parts of hydroxypivalyl hydroxypivalate, 456.6 parts of ε-caprolactone and 0.228 parts of isopropyl titanate were charged in a 2 liter reactor provided with a stirrer, thermostat, thermometer and condenser. The mixture was heated to 150° to 160° C. under nitrogen and the reaction was carried out until the amount of unreacted ε-caprolactone was reduced to less than 1 wt%. The resulting condensate was a light yellow liquid having a hydroxyl value of 259.1 and an acid value of 1.2. The results of molecular weight determination indicated that the hydroxypivalyl hydroxypivalate/ε-caprolactone condensate contained about 2 ε-caprolactone units in average in the molecule. Hereinafter, this condensate will be referred to as "hydroxypivalyl hydroxypivalate/ε-caprolactone condensate (2 M)".

SYNTHESIS EXAMPLE 2

408.4 parts of hydroxypivalyl hydroxypivalate, 684.9 parts of ε-caprolactone and 0.342 parts of isopropyl titanate were charged in the same reactor as in Synthesis Example 1. The reaction was carried out in the same manner as in Synthesis Example 1 until the amount of ε-caprolactone residue was reduced to less than 1 wt%. The resulting condensate was a light yellow liquid having a hydroxyl value of 205.6 and an acid value of 1.5. The results of molecular weight determination indicated that the hydroxypivalyl hydroxypivalate/ε-caprolactone condensate contained about 3 ε-caprolactone units in average in the molecule. Hereinafter, this condensate will be referred to as "hydroxypivalyl hydroxypivalate/ε-caprolactone condensate (3 M)".

PREPARATION OF DI(METH)ACRYLATE ESTERS (GENERAL FORMULA [I])

EXAMPLE 1

432.3 parts of the hydroxypivalyl hydroxypivalate/ε-caprolactone condensate (2 M), 172.9 parts of acrylic acid, 5.2 parts of sulfuric acid, 1.3 parts of hydroquinone, 320 parts of benzene and 80 parts of cyclohexane were charged in a 2 liter reactor provided with a stirrer, thermostat, thermometer, condenser and separator. The mixture was heated. Water formed by the reaction was distilled together with the solvent and condensed, water alone was removed from the reaction system and the solvent was returned into the reactor.

After 36 parts of water was formed, the mixture was cooled. The reaction temperature was 84° to 90° C. The reaction mixture was dissolved in 800 parts of benzene and 200 parts of cyclohexane. The solution was neutralized with a 20% aqueous sodium hydroxide solution and washed with 500 parts of a 20% aqueous common salt solution three times. The solvent was distilled off under reduced pressure to obtain 512 parts of a light yellow liquid having the following properties:

| Specific gravity (25° C.) | 1.068 |
| Viscosity (25° C.) | 03.1 cps |
| Saponification value | 109.3 mgKOH/g |
| Acid value | 1.01 mgKOH/g |
| Refractive index | .4635 (20° C.) |
| NPGDA (neopentyl glycol diacrylate) content | 1.6 wt % |
| Elementary analysis: | |
| C (%) | H (%) |
| 62.12 | 1.30 |

Absorption frequencies of the product according to high resolution nuclear magnetic resonance (NMR) were determined to obtain the following results:

| No. | Absorption frequency (Hz) |
|---|---|
| 1 | 2632.812 |
| 2 | 2605.468 |
| 3 | 2601.562 |
| 4 | 2496.093 |
| 5 | 2488.281 |
| 6 | 966.796 |
| 7 | 958.984 |

-continued

| No. | Absorption frequency (Hz) |
|---|---|
| 8 | 1933.593 |
| 9 | 1927.734 |
| 10 | 1191.406 |
| 11 | 1160.156 |
| 12 | 1126.953 |
| 13 | 1050.781 |
| 14 | 1042.968 |
| 15 | 1035.156 |
| 16 | 964.843 |
| 17 | 960.937 |
| 18 | 642.578 |
| 19 | 523.437 |
| 20 | 511.718 |
| 21 | 425.781 |
| 22 | 382.812 |
| 23 | 369.140 |
| 24 | 333.984 |
| 25 | 326.171 |
| 26 | −1,953 |

In the determination, tetramethylsilane was used as the internal reference and chloroform was used as the solvent. The determination was effected by observation of the coupling of $H^1$ and $C^{13}$—H followed by identification of $C^{13}$ spectra after decoupling. Nos. 10, 11 and 12 show peaks due to the solvent and No. 26 shows a peak due to tetramethylsilane.

EXAMPLE 2

432.3 parts of the hydroxypivalyl hydroxypivalate/ε-caprolactone condensate (2 M), 206.6 parts of methacrylic acid, 17.3 parts of p-toluenesulfonic acid, 1.6 parts of hydroquinone and 460 parts of toluene were charged in the same reactor as in Example 1. The reaction was carried out in the same manner as in Example 1 until 36 parts of water was formed.

The reaction temperature was 105° to 113° C. The reaction mixture was dissolved in 865 parts of toluene. The solution was neutralized with a 20% aqueous sodium hydroxide solution and washed with 600 parts of a 20% aqueous NaCl solution three times. The solvent was distilled off under reduced pressure to obtain 669.8 parts of a light yellow liquid having the following properties:

| | |
|---|---|
| Specific gravity (25° C.) | 1.056 |
| Visocisty (25° C.) | 125.8 cps |
| Saponification value | 481.2 mgKOH/g |
| Acid value | 0.04 mgKOH/g |
| Refractive index | 1.4635 (20° C.) |
| Elementary analysis: | |
| C (%) | H (%) |
| 63.42 | 8.49 |

| Results of determination according to NMR | |
|---|---|
| No. | Absorption frequency (Hz) |
| 1 | 2632.812 |
| 2 | 2605.468 |
| 3 | 2599.609 |
| 4 | 2513.671 |
| 5 | 2505.859 |
| 6 | 2050.781 |
| 7 | 2042.968 |
| 8 | 1886.718 |
| 9 | 1880.859 |
| 10 | 1193.359 |
| 11 | 1162.109 |
| 12 | 1128.906 |
| 13 | 1054.687 |

-continued

| Results of determination according to NMR | |
|---|---|
| No. | Absorption frequency (Hz) |
| 14 | 1048.828 |
| 15 | 1042.968 |
| 16 | 1035.156 |
| 17 | 966.796 |
| 18 | 962.890 |
| 19 | 642.578 |
| 20 | 523.437 |
| 21 | 511.718 |
| 22 | 425.781 |
| 23 | 382.812 |
| 24 | 369.140 |
| 25 | 333.984 |
| 26 | 326.171 |
| 27 | 273.437 |

Nos. 10, 11 and 12 show peaks due to the solvent.

EXAMPLE 3

546.7 parts of the hydroxypivalyl hydroxypivalate/ε-caprolactone condensate (3M), 151.3 parts of acrylic acid, 4.5 parts of sulfuric acid, 1.2 parts of hydroquinone, 400 parts of benzene and 100 parts of cyclohexane were charged in the same reactor as in Example 1. The mixture was heated and the reaction was carried out in the same manner as in Example 1 until 36 parts of water was formed. The reaction temperature was 81° to 87° C. The reaction mixture was dissolved in 720 parts of benzene and 180 parts of cyclohexane. The solution was neutralized with a 20% aqueous sodium hydroxide solution and then washed with 250 parts of a 20% aqueous NaCl solution three times. The solvent was distilled off under reduced pressure to obtain 476.1 parts of a light yellow liquid having the following properties:

| | |
|---|---|
| Specific gravity (25° C.) | 1.0740 |
| Viscosity (25° C.) | 194.9 cps |
| Saponification value | 502.5 mgKOH/g |
| Acid value | 0.02 mg/KOH/g |
| Refractive index | 1.4655 (20° C.) |
| NPGDA (neopentyl glycol diacrylate) content | 0.32 wt % |
| Elementary analysis: | |
| C (%) | H (%) |
| 62.31 | 8.33 |

| Results of determination according to NMR | |
|---|---|
| No. | Absorption frequency (Hz) |
| 1 | 2626.953 |
| 2 | 2601.562 |
| 3 | 2597.656 |
| 4 | 2492.187 |
| 5 | 2490.234 |
| 6 | 2486.328 |
| 7 | 1964.843 |
| 8 | 1960.937 |
| 9 | 1957.031 |
| 10 | 1927.734 |
| 11 | 1923.828 |
| 12 | 1919.921 |
| 13 | 1189.453 |
| 14 | 1158.203 |
| 15 | 1125.000 |
| 16 | 1044.921 |
| 17 | 1037.109 |
| 18 | 1031.250 |
| 19 | 960.937 |
| 20 | 957.031 |
| 21 | 638.671 |
| 22 | 519.531 |

| Results of determination according to NMR | |
|---|---|
| No. | Absorption frequency (Hz) |
| 23 | 505.859 |
| 24 | 419.921 |
| 25 | 378.906 |
| 26 | 363.281 |
| 27 | 330.078 |
| 28 | 322.265 |

Nos. 13, 14 and 15 show peaks due to the solvent.

EXAMPLE 4

A hydroxypivalyl hydroxypivalate/$\epsilon$-caprolactone condensate containing about 4 $\epsilon$-caprolactone units in average in the molecule was synthesized in the same manner as in the synthesis of the above-mentioned hydroxypivalyl hydroxypivalate/$\epsilon$-caprolactone condensates (2 M) and (3 M). This condensate will be referred to as "hydroxypivalyl hydroxypivalate/$\epsilon$-caprolactone condensate (4 M)".

660.8 parts of the hydroxypivalyl hydroxypivalate/$\epsilon$-caprolactone condensate (4 M), 151.3 parts of acrylic acid, 4.5 parts of sulfuric acid, 1.2 parts of hydroquinone, 480 parts of benzene and 120 parts of cyclohexane were charged in the same reactor as in Example 1. The mixture was heated and the reaction was carried out until 36 parts of water was formed in the same manner as in Example 1. The reaction temperature was 81° to 86° C. The reaction mixture was dissolved in 1040 parts of benzene and 260 parts of cyclohexane. The solution was neutralized with a 20% aqueous sodium hydroxide solution and then washed with 400 parts of a 20% NaCl solution three times. The solvent was distilled off under reduced pressure to obtain 661 parts of a light yellow liquid having the following properties:

| | |
|---|---|
| Specific gravity (25° C.) | 1.0760 |
| Viscosity (25° C.) | 270.6 cps |
| Saponification value | 496.4 mgKOH/g |
| Acid value | 0.03 mgKOH/g |
| Refractive index | 1.4675 (20° C.) |
| NPGDA content | 0.17 wt % |
| Elementary analysis: | |
| C (%) | H (%) |
| 62.45 | 8.39 |

| Results of determination according to NMR | |
|---|---|
| No. | Absorption frequency (Hz) |
| 1 | 2626.953 |
| 2 | 2603.515 |
| 3 | 2601.562 |
| 4 | 2597.656 |
| 5 | 2492.187 |
| 6 | 2484.375 |
| 7 | 1964.843 |
| 8 | 1957.031 |
| 9 | 1927.734 |
| 10 | 1923.828 |
| 11 | 1919.921 |
| 12 | 1189.453 |
| 13 | 1158.203 |
| 14 | 1125.000 |
| 15 | 1044.921 |
| 16 | 1037.109 |
| 17 | 1031.250 |
| 18 | 1017.578 |
| 19 | 960.937 |
| 20 | 957.031 |
| 21 | 931.640 |
| 22 | 536.718 |
| 23 | 519.531 |
| 24 | 507.812 |
| 25 | 480.468 |
| 26 | 419.921 |
| 27 | 378.906 |
| 28 | 363.281 |
| 29 | 330.078 |
| 30 | 326.171 |
| 31 | 322.265 |

Nos. 12, 13 and 14 show peaks due to the solvent.

Table 1 given below shows viscosity, PII (primary irritation index), hardening rate and flexing properties of the di(meth)acrylate esters prepared as described above. For comparison, the data of 1,6-hexanediol diacrylate, neopentyl glycol diacrylate and pentaerythrithol triacrylate are also shown.

Test methods

The test methods for obtaining the data were as follows:

PII (Primary irritation index)

Di(meth)acrylate esters were used in the determination of PII. The measurement was carried out in Huntingdon Research Centre (Huntingdon Cambs., PE 18 6ES, England).

Outline of the method

Six white strain rabbits were used. Hair was removed with electric clippers. A 0.5 ml aliquot of a sample was applied to a part of each rabbit. The rabbits were fixed and the sample was applied batchwise to the site (side of the spine on the back). Immediately thereafter, the body including the site was covered with an impermeable substance such as rubber or cloth for 24 h. Then, the pad was removed and the dermal reactions at the site were assessed according to the dermal reaction standard.

After 72 h, the dermal reactions were again assessed. The sample was also applied to the skin having minor incisions through the stratum corneum in the same manner as in the treatment of the intact skin. Care was taken so that these incisions were not deep enough to disturb the dermis or cause bleeding. The skin with incisions was also assessed after 24 h and 72 h. The subtotal of erythema and eschar formation on the intact skin and abraded skin after 24 and 72 h was added to the subtotal of oedema formation and the total was divided by 4 to obtain a score per animal. Then, the average of the score of 6 animals was calculated. The resulting value is the average primary irritation index.

| Dermal reaction standard | |
|---|---|
| Erythema and eschar formation: | |
| No erythema | 0 |
| Very slight erythema (barely perceptible) | 1 |
| Well-defined erythema | 2 |
| Moderate to severe erythema | 3 |
| Severe erythema (beet redness) to slight eschar formation (injuries in depth) | 4 |
| Oedema formation: | |
| No oedema | 0 |

| Dermal reaction standard | |
|---|---|
| Very slight oedema (barely perceptible) | 1 |
| Slight oedema (edges of area well-defined by definite raising) | 2 |
| Moderate oedema (raising of approximately 1 mm) | 3 |
| Severe oedema (raising of more than 1 mm and extending beyond the area of exposure) | 4 |

As for the above experiments, refer to "Methods for the Study of Irritation and Toxicity of Substances Applied Topically to the Skin and Mucous Membranes" by Draize, Horn H., Woodard, Geoffrey and Calvery, Herbert O., [J. Pharm. & Exp. Ther. 82, 337 (1944)].

The data of hardening rate and flexing properties were obtained by dissolving the new di(meth)acrylate esters obtained in Examples 1 to 4, 1,6-hexanediol diacrylate, neopentyl glycol diacrylate, and pentaerythritol triacrylate in a resin obtained by esterifying epoxy acrylate resin [Epikote 828 (bisphenol-type epoxy resin of Shell International Chemicals Corp.)] with acrylic acid, then adding 5 wt%, based on the respective dissolved matters, of Irgacure 651 (a product of Ciba-Geigy Co.) as a sensitizer, applying the mixture to a polyvinyl chloride sheet by means of a roll coater to form a film having 25μ thickness and curing the film by U.V. rays using a high pressure mercury lamp (a product of Toshiba Co.; 2 kw).

Curing rate

The number of times of passing of the film 8 cm below the high pressure mercury lamp at a rate of 18 m/min until the film became tack-free.

Flexing properties

A cross-linked, hardened film was formed on the surface of a polyvinyl chloride sheet. Rectangular test pieces having 10 mm width and 6 cm length were cut out from the sheet. A cylindrical rod having a diameter of 10, 8, 6, 4, 3 or 2 mm) was placed on the center of each sample and the sample was bent at an angle of 180° C. Diameter of the rod which caused the cracks was examined. The smaller diameter is preferable.

TABLE 1

| No. | Resin (wt %) | Monomer (wt %) | Sensitizer (%) | Monomer viscosity (25° C. cps) | PII (Primary irritation index) | Curing rate (number of passing times) | Flexing properties |
|---|---|---|---|---|---|---|---|
| 1 | Epoxy acrylate (50) | 1,6-hexanediol diacrylate (50) | Irgacure-651 (5) | 4 ~ 6 | 6.2 | 3 | 4 |
| 2 | Epoxy acrylate (50) | Neopentyl glycol diacrylate (50) | Irgacure-651 (5) | 5 ~ 6 | 4.96 | 4 | 3 |
| 3 | Epoxy acrylate (30) | Pentaerythritol triacrylate (70) | Irgacure-651 (5) | 500 ~ 800 | 2.5 | 2 | 6 |
| 4 | Epoxy acrylate (50) | Product of Example 1 (50) | Irgacure-651 (5) | 103.1 | 0.1 | 3 | less than 2 |
| 5 | Epoxy acrylate (50) | Product of Example 2 (50) | Irgacure-651 (5) | 125.8 | — | 7 | less than 2 |
| 6 | Epoxy acrylate (50) | Product of Example 3 (50) | Irgacure-651 (5) | 194.9 | — | 3 | less than 2 |
| 7 | Epoxy acrylate (50) | Product of Example 4 (50) | Irgacure-651 (5) | 270.6 | 0.3 | 3 | less than 2 |

What is claimed is:

1. Di(meth)acrylate esters of the formula [I]:

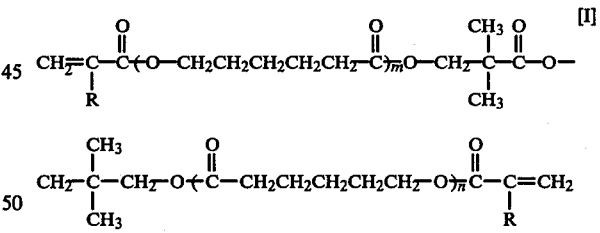

wherein m and n each represents 0 or an integer of 1 to 3, the average sum of m+n being 1 to 6, and R represents hydrogen or a methyl group.

2. Diacrylate esters according to claim 1 wherein R is hydrogen

3. Di(meth)acrylate esters according to claim 1 wherein the average sum of m+n is about 2.

4. Di(meth)acrylate esters according to claim 1 wherein the average sum of m+n is about 3.

5. Di(meth)acrylate esters according to claim 1 wherein the average sum of m+n is about 4.

* * * * *